(12) United States Patent
Powers

(10) Patent No.: US 6,441,582 B1
(45) Date of Patent: Aug. 27, 2002

(54) BATTERY ARRANGEMENT FOR IMPROVED DEFIBRILLATOR SAFETY

(75) Inventor: Daniel J Powers, Issaquah, WA (US)

(73) Assignee: Koninklijke Phillips Electronics N.V., Eindhoven (NL)

( * ) Notice: Subject to any disclaimer, the term of this patent is extended or adjusted under 35 U.S.C. 154(b) by 0 days.

(21) Appl. No.: 09/538,014

(22) Filed: Mar. 29, 2000

(51) Int. Cl.⁷ .............................. N02J 7/00; A61N 1/18
(52) U.S. Cl. ........................................ 320/112; 607/5
(58) Field of Search .................... 607/4, 5, 9; 320/112

(56) References Cited

U.S. PATENT DOCUMENTS

| | | | |
|---|---|---|---|
| 5,262,710 A | * 11/1993 | Taylor | 320/110 |
| 5,483,165 A | 1/1996 | Cameron | |
| 5,560,999 A | * 10/1996 | Pedicini et al. | 429/27 |
| 5,803,927 A | 9/1998 | Cameron et al. | |
| 5,836,978 A | 11/1998 | Gliner et al. | |
| 6,304,779 B1 | * 10/2001 | Yerkovich | 607/5 |

OTHER PUBLICATIONS

Samuel C. Levy. "Battery Hazards and Accident Prevention", 1994, pp. 189–193.

* cited by examiner

Primary Examiner—Gregory Toatley
(74) Attorney, Agent, or Firm—Tony Piotrowski

(57) ABSTRACT

A reliable battery module that is safe is of critical importance to battery operated medical devices. This invention limits the amount of active materials in each cell of a battery module. Limiting the amount of active materials in each cell increases the safety and reliability of the battery module by minimizing the effect of a damaged or defective cell on the battery module output and on the potential hazard that such a cell can cause.

18 Claims, 5 Drawing Sheets

BATTERY ARRANGEMENT FOR IMPROVED DEFIBRILLATOR SAFETY

FIELD OF THE INVENTION

The invention is directed towards batteries, in particular, batteries used in battery operated devices. The invention relates to battery arrangements that result in safe and reliable operation of battery powered devices. This invention may be used with external defibrillators, including automatic or semi-automatic external defibrillators ("AEDs"), manual defibrillators and defibrillator trainers.

BACKGROUND

Battery operated devices find diverse applications ranging from small and simple children's toys to sophisticated laptop computers and large electric powered vehicles. When batteries are used in medical devices, such as automatic or semiautomatic external defibrillators (AEDs), manual defibrillators, the performance of the batteries may determine whether a patient lives or dies. An example of an AED that uses batteries is described in Cameron et al., U.S. Pat. No. 5,803,927 entitled "Electrotherapy Method and Apparatus for External Defibrillation," the specification of which is incorporated herein.

A typical battery cell includes an anode, a cathode, an electrolyte and a housing. A chemical reaction takes place between the anode and cathode. The anode and the cathode have different tendencies to gain or lose electrons. This difference in electron affinity in harnessed in a chemical reaction to accomplish useful work. The amount of work or energy available depends on the magnitude of the electron affinity difference and quantity of the anode and cathode materials available for the chemical reaction. The difference in affinity is a function of the battery chemistry of the battery cell.

There are many factors to consider when choosing battery chemistry, the type of active materials used for the anode and cathode as well as the electrolyte composition, for a particular application. These include voltage, current, and capacity requirements of the battery operated device, in addition to weight, cost, shelf life, toxicity, recyclability, and operating temperature range. A non-rechargeable battery, also referred to as a primary battery, is discarded at the end of its operational life. A rechargeable battery, also referred to as a secondary battery, is recharged after discharge throughout its operational use. Once a battery chemistry is chosen, a number of individual cells having the same voltage and capacity may be connected in series, parallel, or series and parallel to form a battery module. In designing a battery module to obtain the required capacity, it is common practice to use fewer cells of larger capacity, that is cells with larger quantities of active materials to reduce the total weight and cost of the battery module.

Cameron et al. discusses battery reliability in U.S. Pat. No. 5,483,165 entitled "Battery System and Method for Determining a Battery Condition," the specification of which is incorporated herein. Cameron discloses a battery monitor and capacity indicator that uses a sense cell to determine the remaining capacity and depletion condition of the main battery.

Reference should be made to the detailed description of the preferred embodiments.

Operator safety and power source reliability is of critical importance for any battery module, but even more so if it powers a medical device. When a battery module is assembled it is common practice that external safety devices, such as electrical fuses and thermal switches, are incorporated. These safety devices limit the current and temperature of the battery cells, but do not necessarily protect against an internal short circuit, a rapid change in the chemical reaction, or severe mechanical stress. A safety vent internal to the battery cell serves to protect against these faults by venting its contents to shut down the chemical reaction and relieve internal pressure and temperature build-up. However, in some instances and under some conditions, the cell can not vent quickly enough to prevent the cell from exploding or rupturing. In addition, some battery chemistries vent hazardous products, which may be any combination of reactive, corrosive, toxic, and flammable. The battery module output can deteriorate and there is a danger of explosion and fire due to heat generation or ignition. This can result in an unsafe situation for the operator and others in the vicinity of the device, particularly when used in a confined space, such as in an airplane. This can also result in the failure of the device, which in the case of a medical device may result in patient death. There have been instances of battery modules rupturing in medical devices which resulted in physical injury. Therefore, what is needed is a reliable battery module that maximizes safety for medical emergency use.

SUMMARY

This invention is directed to a battery module capable of delivering greater than 1 KiloJoule (KJ), comprising more than 6 lithium cells, each lithium cell containing either less than 2.0 grams of lithium or less than 10.0 grams of manganese dioxide, electrically connected in series, parallel, or both series and parallel. The battery module may be either primary or secondary. In another embodiment, the battery module is capable of delivering greater than 85 KJ, comprising a plurality of lithium cells, each lithium cell containing either less than 2.0 grams of lithium or less than 10.0 grams of manganese dioxide, electrically connected in series, parallel, or both series and parallel. The battery module may be either primary or secondary. In yet another embodiment, the battery module is capable of delivering less than 84 KJ, comprising a plurality of lithium cells, each lithium cell containing either less than 2.0 grams of lithium or less than 10.0 grams of manganese dioxide, electrically connected in series, parallel, or both series and parallel. The battery module may be either primary or secondary.

In another embodiment, an external defibrillator, comprising a battery module capable of delivering greater than 1 KJ throughout its operational life, including, more than 6 lithium cells, each lithium cell containing either less than 2.0 grams of lithium or less than 10.0 grams of manganese dioxide, electrically connected in series, parallel, or both series and parallel. The battery module provides power to the external defibrillator. In a preferred embodiment, the external defibrillator delivers a biphasic waveform to a patient. The battery module may be either primary or secondary. In another embodiment, an external defibrillator comprising a battery module capable of delivering greater than 85 KJ throughout its operational life, including, a plurality of lithium cells, each lithium cell containing either less than 2.0 grams of lithium or less than 10.0 grams of manganese dioxide, electrically connected in series, parallel, or both series and parallel. The battery module provides power to the external defibrillator. In a preferred embodiment, the external defibrillator delivers a biphasic waveform to a patient. The battery module can be either primary or secondary. In yet another embodiment, an external defibrillator, comprising a battery module capable of delivering less than 84 KJ, including, a plurality of lithium cells, each lithium cell containing either less than 2.0 grams of lithium or less than 10.0 grams of manganese dioxide, electrically connected in series, parallel, or both series and parallel. The battery module provides power to the external defibrillator. In a preferred embodiment, the external defibrillator delivers a biphasic waveform to a patient. The battery module can be either primary or secondary.

Another embodiment of this invention is a battery module capable of delivering greater than 1 KJ throughout its operational life, comprising a plurality of lithium cells, each lithium cell containing either less than 21 grams of sulfur dioxide or less than 15 grams of thionyl chloride, electrically connected in series, parallel, or both series and parallel. In yet another embodiment, an external defibrillator, comprising a battery module capable of delivering greater than 1 KJ throughout its operational life, including, a plurality of lithium cells, each lithium cell containing either less than 21 grams of sulfur dioxide or less than 15 grams of thionyl chloride, electrically connected in series, parallel, or both series and parallel. The battery module provides power to the external defibrillator. Preferably, the external defibrillator delivers a biphasic waveform to a patient.

An embodiment of this invention is a method of optimizing a battery module, including a plurality of cells, for safe operation, comprising the steps of: determining voltage and capacity requirements; determining if primary or secondary battery cells should be used; determining a battery chemistry for the battery cells; determining the quantity of active material in the battery cell; and determining the number of cells to be electrically connected in series, parallel, or both series and parallel.

For a full understanding of the present invention, reference should be made to the detailed description of the preferred embodiments and to the accompanying drawings. However, other features and advantages of the present invention will be apparent to persons of skill in the art from the following description of the preferred embodiments, and from the claims.

DETAILED DESCRIPTION OF THE PREFERRED EMBODIMENTS

Figure 1:
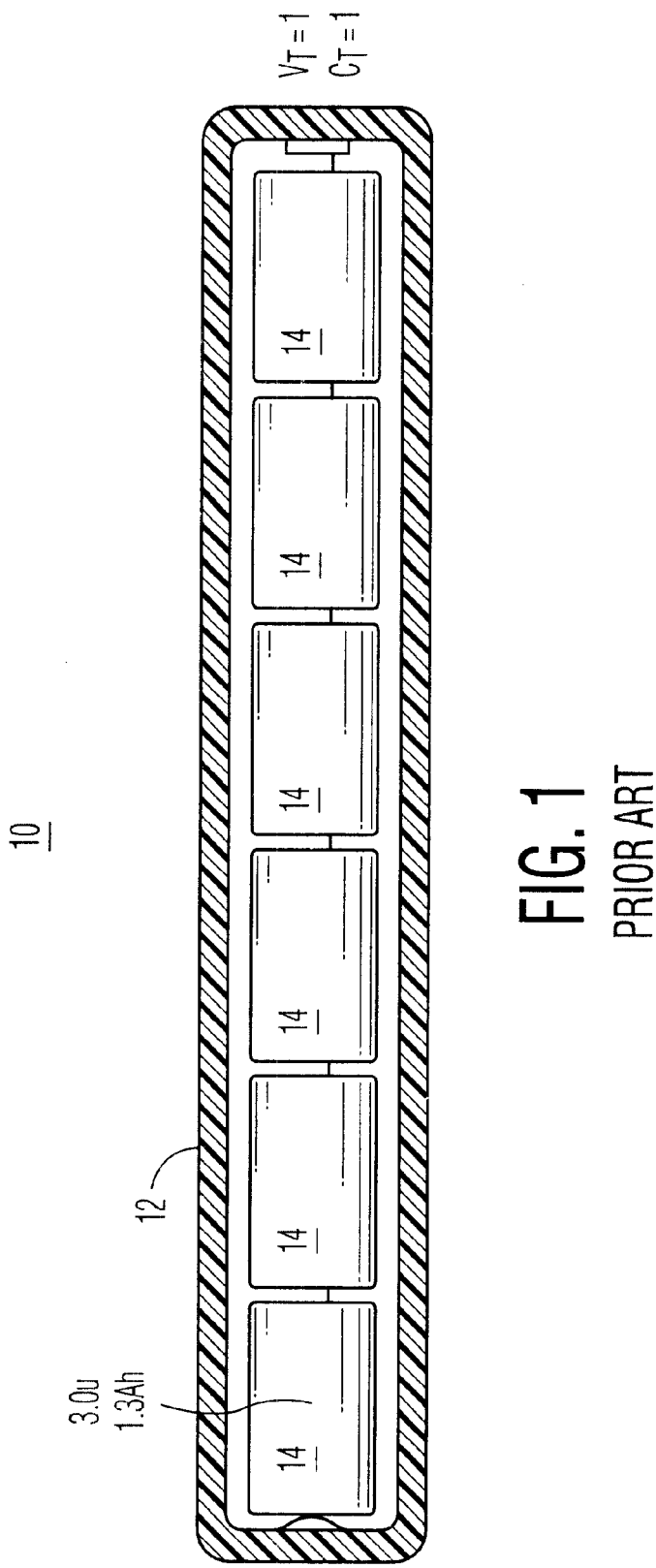
FIG. 1 is a cross sectional view of a battery module housing (prior art).

The following discussion is presented to enable a person skilled in the art to make and use the invention. Various modifications to the preferred embodiment will be readily apparent to those skilled in the art, and the generic principles herein may be applied to other embodiments and applications without departing from the spirit and scope of the present invention as defined by the appended claims. Thus, the present invention is not intended to be limited to the embodiments shown, but is to be accorded the widest scope consistent with the principles and features disclosed herein.

A battery cell delivers a certain amount of energy throughout its operational life. The amount of energy that the battery cell can deliver depends on many factors related to the battery and to the device it powers. Factors relating to the battery include: the battery chemistry, the quantity of active materials in the cell, and the cell design. Factors relating to the battery operated device include: the minimum voltage that the device will still operate, the rate at which the energy is discharged from the battery, and the temperature at which the device is operated. Also, a safety margin is designed into the device where low batteries are indicated but the device still functions.

Battery capacity is a measure of the total energy contained in the battery. Battery capacity is specified in Ampere hours (Ah). The battery capacity in Joules (J) is the product of the battery capacity in Ah and the battery voltage in Volts (V), multiplied by 3600. If a user needs to power a device requiring a voltage $V_T$ and a capacity of $C_T$Ah, individual cells with a voltage $V_c$ and a capacity $C_c$ may connected in series and parallel to obtain the required output. The voltage $V_T$ of a battery module with N cells in series, each cell of voltage $V_c$, is:

$$V_T = N\ V_c \qquad (1)$$

The capacity $C_T$ of a battery module with M cells in parallel, each cell of capacity $C_c$, is:

$$C_T = M\ C_c \qquad (2)$$

Conventional wisdom dictates using cells of larger capacity and higher voltage to minimize the number of cells in parallel M and minimize the number of cells in series N so that the weight and cost of the battery module is minimized.

In practice, battery operated devices may only draw a fraction $f_h$ of the total energy contained in the battery before battery replacement or recharge is necessary. For example, on AEDs only 20 to 50% of the batteries' rated capacity may actually be delivered to the defibrillator before battery replacement or recharge is necessary. In addition, not all the battery energy delivered to the defibrillator is delivered from the defibrillator to the patient. This depends on the efficiency of the defibrillator, the ratio $\eta_d$ of energy delivered to the patient to the required battery energy, and may vary between 50–80%. For example, an AED that delivers monophasic waveforms may need 600 J of battery energy to deliver a 360 J shock to the patient, that is a defibrillator efficiency of $\eta_d$=0.60. An AED that delivers biphasic waveforms may need 220 J of battery energy to deliver a 150 J shock to the patient, that is a defibrillator efficiency of $\eta_d$=0.68. Thus, for an AED, the battery capacity $C_h$ necessary for delivering P shocks of energy $E_s$ to the patient before the battery module is replaced or recharged is:

$$C_h = PE_s / f_h \eta_d \qquad (3)$$

Thus, for illustrative purposes, a battery module in a biphasic AED designed to deliver 100 shocks before the battery module is replaced or recharged may require a battery capacity of 84 KJ (with $f_h$=0.26) or 23 Watt hours (Wh) or 1.3 Ah with a battery module voltage of 18 V. An AED using the monophasic technology requires about 3 times more battery energy per shock, a battery capacity of about 3.6 Ah at 18V may be necessary. A battery module capable of delivering 1 KJ throughout its operational life or between recharge could supply a biphasic AED with enough energy for at least one shock.

The battery module needs to deliver its energy to the defibrillator in a clinically reasonable amount of time, for instance 10 seconds, so that the patient can be shocked successively without long delays during the time critical defibrillation procedure. For the monophasic AED, 600J/10 sec or 60 Watts (W) are needed for a shock. For the biphasic AED, 220J/10 sec or 22 W are needed for a shock. Thus the monophasic AED requires battery modules of high capacity and high power. This combination of high capacity and high power has contributed to prior art battery modules with reduced safety. A biphasic AED is described in Gliner et al., U.S. Pat. No. 5,836,978 entitled "Electrotherapy Method for Producing a Multiphasic Discharge Based Upon a Patient-Dependent Electrical Parameter and Time," the specification of which is incorporated herein. The biphasic defibrillation technology delivers similar performance to the monophasic defibrillator without the higher power and capacity requirements.

Lithium batteries have a high energy output due to the use of elemental lithium as the anode. Lithium has the highest electrode potential and is the lightest of all metals producing the highest energy capacity per unit of weight. Lithium batteries describe a family of battery chemistries that use lithium as the active material for the anode and uses different active materials for the cathode, as well as different electrolyte and cell designs. For instance, iodine $I_2$ can form a solid cathode and uses a solid electrolyte. Other solid cathode systems, using a liquid electrolyte include manganese dioxide $MnO_2$, poly-carbonmonoflouride CF, silver chromate $AgCrO_4$, iron disulfide $FeS_2$, and copper oxide CuO. Other liquid cathode systems, using a liquid electrolyte include sulfur dioxide $SO_2$, thionyl chloride $SOCl_2$, and sulfuryl chloride $SO_2Cl_2$. Each of these battery chemistries has an individual electrical characteristic, energy density, operating temperature limit, discharge rate limit, reliability, shelf life, and safety. For example, the lithium thionyl chloride system has a higher voltage, higher energy density, wider operating temperature limit, and longer shelf life than other lithium batteries. However, thionyl chloride is reactive, corrosive, and toxic. An example of a lithium thionyl chloride ($Li/SOCl_2$) battery cell is LS14500 AA size cell (manufactured by SAFT America, Inc.) where each cell has a voltage of 3.6 Volts, a capacity of 2.1 Amp hour (Ah), and each cell contains less than about 15 grams of $SOCl_2$. The solid cathode systems of the lithium battery are less volatile than the liquid electrode systems.

Lithium-ion batteries are secondary (rechargeable). The battery chemistry of a lithium-ion cell may include a carbon C anode, a lithium cobaltate $LiCoO_2$ cathode, and an organic liquid electrolyte. An example of a lithium-ion battery is a NP-F730 manufactured by Sony Energytec, Inc.

A typical battery operated device may use a single cell or a single string of 26 cells in series. FIG. 1 is a cross sectional view of a prior art battery module 10 and a housing 12 containing a single string of six cells 14 in series. The housing 12 can be external to the battery operated device as is shown in FIG. 1 or the housing can be internal to the battery operated device (not shown). An example of suitable cells 14 that can be utilized are ⅔ A size cells 14 of lithium manganese dioxide ($Li/MnO_2$), wherein each cell 14 has a voltage of 3.0 Volts, and a capacity of 1.3 Ah. Other cells 14 that would be appropriate would be obvious to one skilled in the art. This prior art battery module 10 has a voltage of 18.0 Volts and a capacity of 1.3 Ah or 84 KJ. This prior art battery module 10 has enough energy to deliver 100 shocks when used in a biphasic AED.

Battery cells 14 of lithium manganese dioxide ($Li/MnO_2$) are available in larger sizes, for example U256OH ¾ C size cells 14 (manufactured by Ultralife® Batteries, Inc.) where each cell 14 has a voltage of 3.0 Volts, a capacity of 5.6 Amp hour (Ah), and each cell 14 contains about 2.0 grams of Li and about 10 grams of $MnO_2$.

Figure 2A:
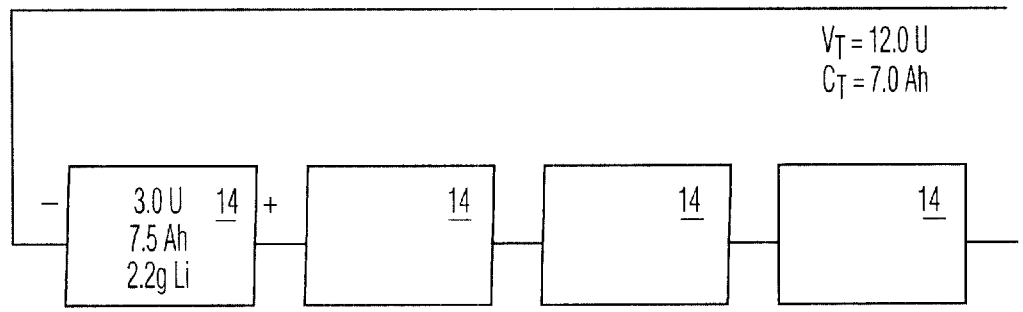
FIG. 2A is a block diagram of a battery module (prior art).

FIG. 2A shows a block diagram of an example of a prior art battery module 10 made of a single chain of four D size cells 14 of lithium sulfur dioxide ($Li/SO_2$) connected in series. An example of suitable cells 14 that can be utilized are LO26SHX D size cells 14 (manufactured by Saft America, Inc.) where each cell 14 has a voltage of 3.0 Volts, a capacity of 7.0 Amp hour (Ah), and each cell 14 contains about 2.2 grams of Li and less than about 21 grams of $SO_2$. Other cells 14 that would be appropriate would be obvious to one skilled in the art. The battery module 10 has an output with a voltage of 12.0 Volts and a capacity of 7.0 Ah or 302 KJ.

Figure 2B:
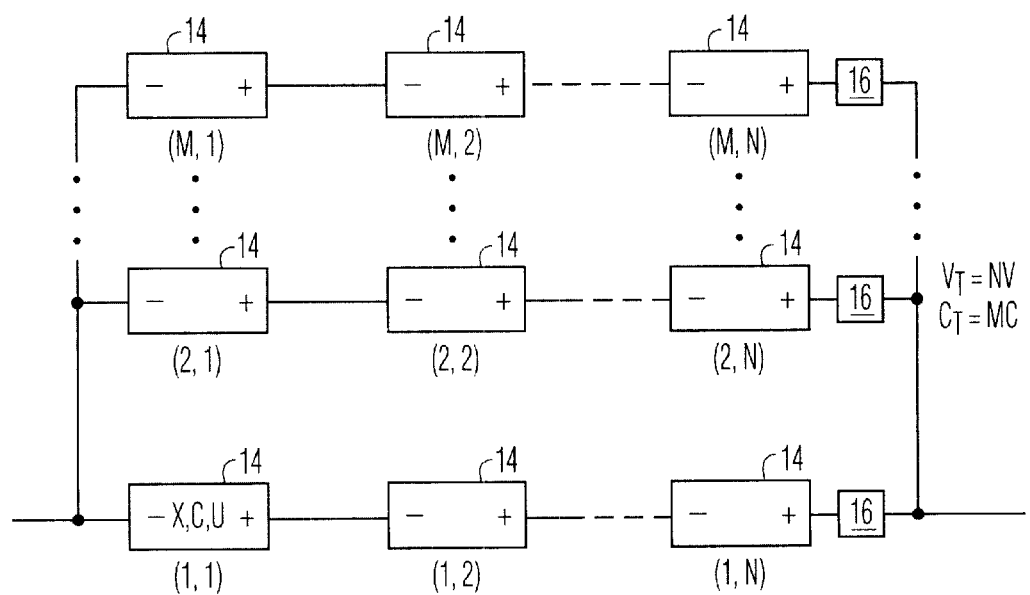
FIG. 2B is a block diagram of a generalized battery module of FIG. 2A (prior art).

The battery module 10 described above in FIG. 2A can be generalized. FIG. 2B shows a block diagram of a generalized prior art battery module 10 made of cells 14 each containing X amount of active material, having a capacity C, and a voltage V. There are N cells 14 in series and M cells 14 in parallel. There is a current blocking device 16 connected in series with each of the M parallel strings to prevent a reverse current or charging condition from another parallel string in the battery module 10. The current blocking device 16 can be a diode with anode connected to the positive side of the string being protected and the cathode connected to the positive output. The battery module 10 has an output with a voltage of $V_T$=NV and a capacity of $C_T$=MC.

Figure 3A:
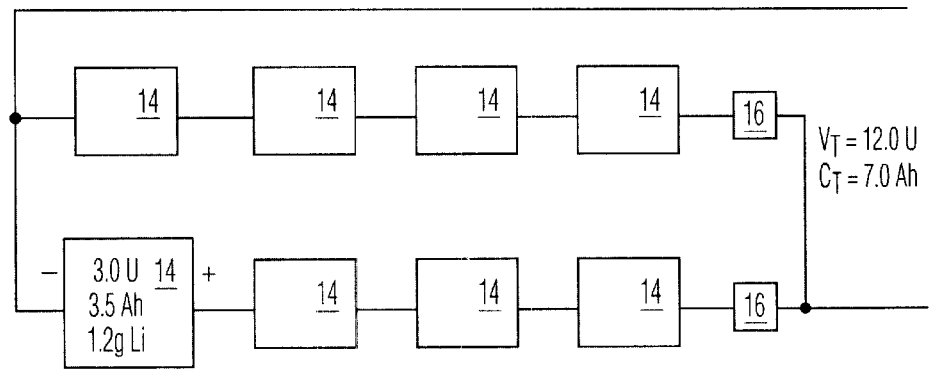
FIG. 3A is a block diagram of a battery module according to one embodiment of the present invention that uses the same battery chemistry as in FIGS. 2A and 2B.

FIG. 3A shows a block diagram of a battery module 10 constructed according to one embodiment of the present invention. This battery module 10 would replace the prior art battery module 10 of FIG. 2A and is made of two parallel chains of four C size cells 14 of $Li/SO_2$ connected in series. There is a current blocking device 16, connected in series with each of the two parallel strings to prevent a reverse current or charging condition from another parallel string in the battery module 10. A suitable current blocking device 16 is, for example, a diode. Importantly the current blocking device 16 can be located within a battery housing, and thus proximate to the battery cells 14, or it can be located in the receiving device housing. An example of suitable cells 14 that can be utilized are LO29SHX C size cells 14 (manufactured by Saft America, Inc.) where each cell 14 has a voltage of 3.0 Volts, a capacity of 3.5 Ah, and contains about 1.2 grams of Li and less than about 10 grams of sulfur dioxide $SO_2$. Other cells 14 that would be appropriate would be obvious to one skilled in the art. This battery module 10 has an output with a voltage of 12.0 Volts and a capacity of 7.0 Ah or 302 KJ similar to the previous example and contains nearly the same total amount of sulfur dioxide $SO_2$, less than about 80 grams, the difference is that each individual cell 14 contains about half the amount of active $Li/SO_2$ materials. If a cell 14 becomes defective or otherwise develops a problem, the potential damage incurred corresponds to the quantity of active materials it contains. Thus, the greater the amount of active materials in a cell 14 the greater the potential hazard. The small capacity cell 14 of FIG. 3A will leak less active material, vent less gas and generate less heat than the large capacity cell 14 of FIG. 2A and reduce the chance and magnitude of an explosion or fire. Importantly, for a battery module 10 with many cells 14, the effect of one bad cell 14 on its output is reduced.

In the example above, sulfur dioxide $SO_2$ would be vented. Sulfur dioxide $SO_2$ has a Occupational Safety and Health Administration (OSHA) permissible exposure limit (PEL) of 5 parts per million (ppm) and a American Conference of Governmental and Industrial Hygienists (ACGIH) threshold limit value (TLV) of 2 ppm. Sulfur dioxide $SO_2$ has a lethal concentration low "LCLO", the lowest concentration of a material in the air capable of killing a specified species over a specified time, for human inhalation (IHL-HMN LCLO) of 1000 ppm/10 minutes. Sulfur dioxide $SO_2$ also has a lethal concentration 50 "LC50", the concentration of a material in the air found to be lethal in 50% of a group of test animals exposed for the specified time period (IHL-RAT LC50), of 2520 ppm/1 hour. Lithium metal does not have an established OSHA PEL or ACGIH TLV value. Lethal dose 50 (LD50) is the dose found to be lethal in 50% of a group of test animals when administered by a specified route. Lithium has a (LD50) of 1000 mg/kg administered intraperitoneally to mice.

It is well known in the art that the greater the amount of anode material used in a cell 14, the greater the amount of cathode material is necessary to sustain the chemical reaction. Therefore, limiting the amount of lithium in a cell 14 will also limit the amount of cathode material used in a cell 14.

Figure 3B:
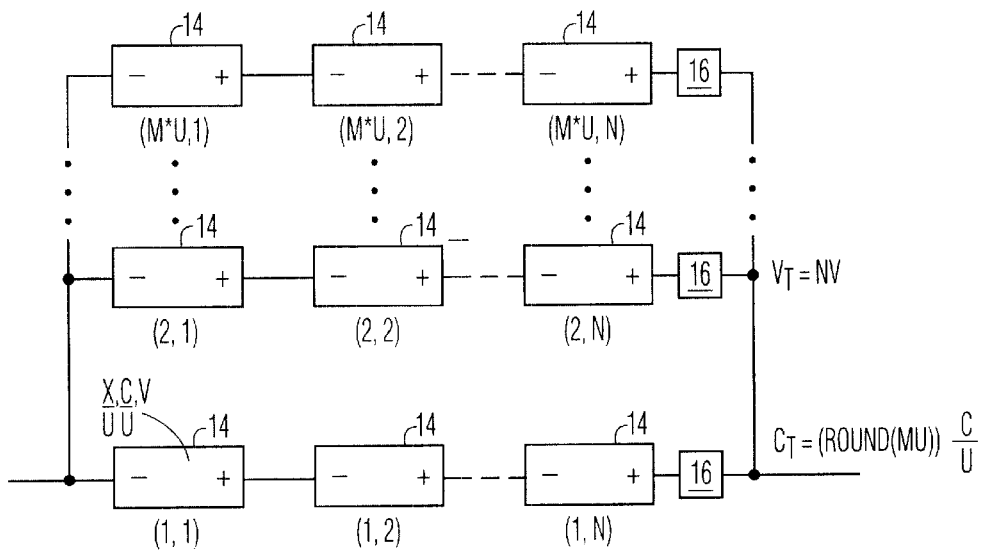
FIG. 3B is a block diagram of a generalized battery module according to the embodiment of FIG. 3A.

FIG. 3B shows a block diagram of a generalized battery module 10 constructed according to the embodiment of the present invention shown in A FIG. 3A. This battery module 10 would replace the battery module 10 of FIG. 2B and is made of cells 14 each containing a fraction X/U of active material, having a capacity of approximately C/U, and a voltage V, where U is greater than 1. There are N cells 14 in series and the rounded integer value of M*U cells 14 in parallel. The rounded integer value may have been rounded up or down depending on the size of the remainder. There is a current blocking device 16, connected in series with each of the parallel strings. A suitable current blocking device 16 is, for example, a diode. As mentioned previously, the current blocking device 16 can be located within a battery housing, and thus proximate to the battery cells 14, or it can be located in the receiving device housing. The battery module 10 has an output with a voltage of $V_T=NV$ and a capacity of $C_T=$(round MU)(C/U).

Figure 4A:
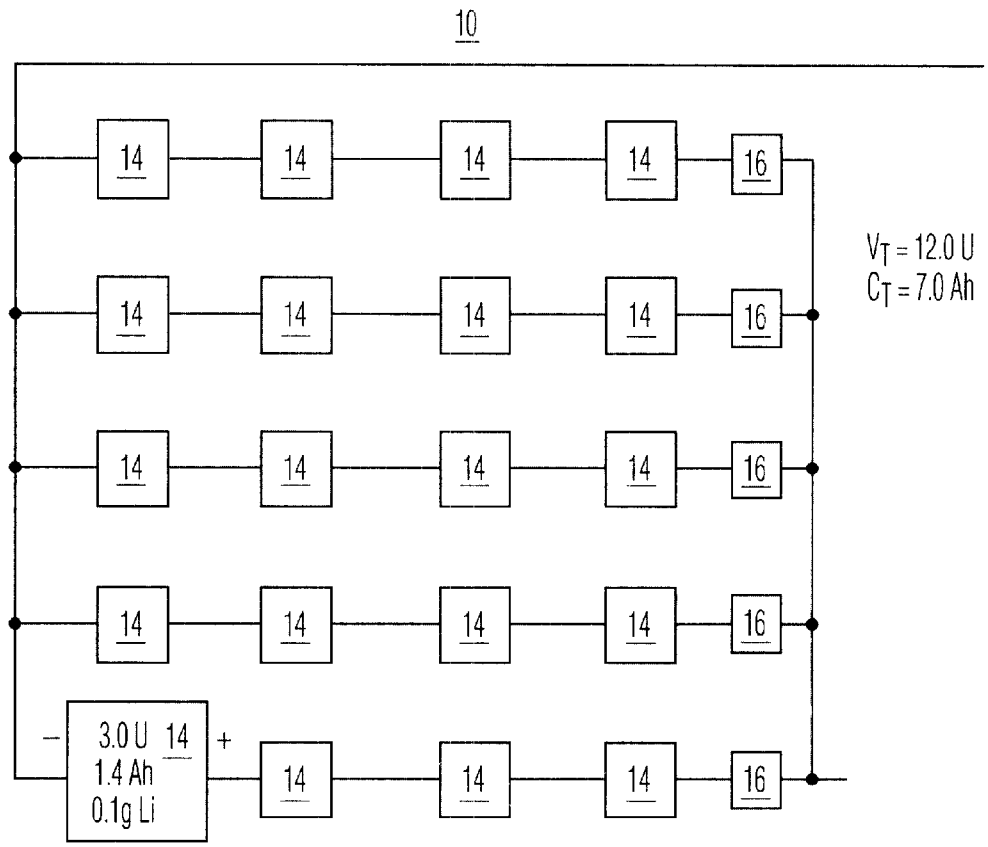
FIG. 4A is a block diagram of a battery module according to another embodiment of the present invention that uses a battery chemistry different than that of FIGS. 2A and 2B.

FIG. 4A shows a block diagram of a battery module 10 constructed according to another embodiment of the present invention. This battery module 10 would also replace the prior art battery module 10 of FIG. 2A and could take advantage of a different battery chemistry. This different battery chemistry may, for instance, be safer and more stable, such as a lithium battery chemistry utilizing a solid cathode material. Reducing the capacity of the battery cell 14 sometimes allows for the use of safer and more stable battery chemistries. This battery module 10 can be five parallel chains of four ⅔ A size cells 14 of lithium manganese dioxide ($Li/MnO_2$). There is a current blocking device 16, connected in series with each of the five parallel strings to prevent a reverse current or charging condition from another parallel string in the battery module 10. A suitable current blocking device 16 is, for example, a diode. Again, the current blocking device 16 can be located within a battery housing, and thus proximate to the battery cells 14, or it can be located in the receiving device housing.

An example of cells 14 that can be utilized are Duracell® DL123A (manufactured by Duracell, Inc.) ⅔ A size cells 14 each cell 14 has a voltage of 3.0 Volts, a capacity of 1.4 Ah, and each cell 14 contains about 0.1 grams of Li and about 1 gram of manganese dioxide $MnO_2$. Other cells 14 that would be appropriate would be obvious to one skilled in the art. This battery module 10 has a voltage of 12.0 Volts and a capacity of 7.0 Ah or 302 KJ.

Manganese dioxide $MnO_2$ has an OSHA PEL of 5 mg/cubic meter ceiling, the maximum allowable exposure limit, and a ACGIH TLV of 0.2 mg/cubic meter time weighted average (TWA). Manganese dioxide $MnO_2$ has an oral lethal dose in 50% of test animals ORL-RAT LD50 of greater than 3478 mg/kg. In contrast to the lithium sulfur dioxide $Li/SO_2$ battery cell 14, the lithium manganese dioxide $Li/MnO_2$ cell 14 is safely used in millions of consumer applications including cameras and wristwatches. The lithium magnesium dioxide $Li/MnO_2$ battery cell 14 meets the U.S. Environmental Protection Agency (EPA) Toxicity Characteristic Leaching Procedure (TCLP) and may be disposed of with normal waste without a complicated recycling process. The lithium sulfur dioxide $Li/SO_2$ battery cell 14 must be manually disabled by the user prior to disposal.

The high volume production of the lithium manganese dioxide $Li/MnO_2$ battery cells 14 for consumer applications ensures a large knowledge base and strict quality control of the chemistry and manufacture of the battery cells 14 by the manufacturers. Additional safety features may be found on consumer grade battery cells, for example, the Duracell® DL123A cell has an internal positive temperature coefficient (PTC) device that protects the cell against short circuits or discharge currents above its design limits.

Figure 4B:
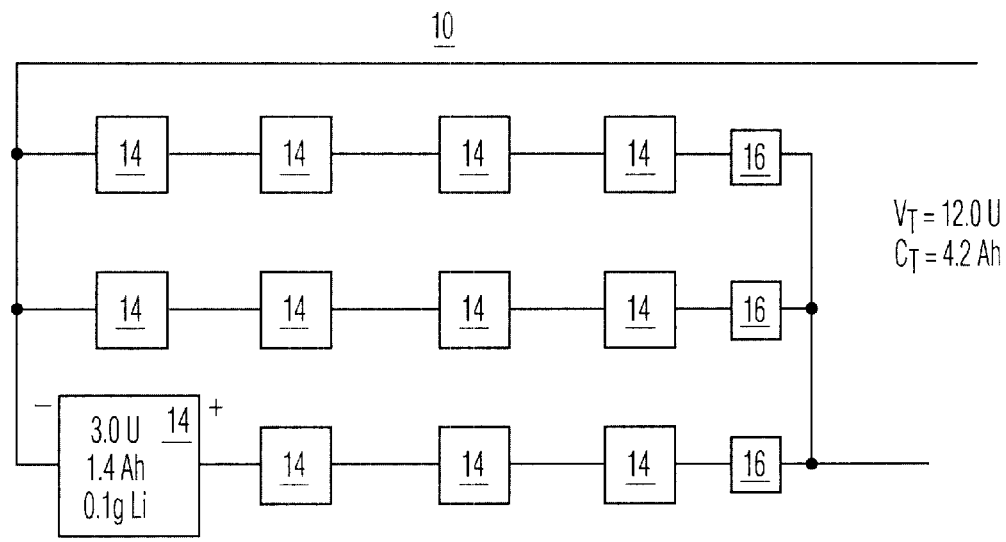
FIG. 4B is a block diagram of a battery module according to the preferred embodiment of the present invention that uses a battery chemistry of FIG. 4A.

FIG. 4B shows a preferred embodiment of the present invention. This embodiment combines the biphasic technology with the present invention. The battery module 10 of FIG. 4B is lower capacity and lower power than the battery module 10 of FIG. 4A while still using the cells with the safer battery chemistry and smaller quantities of active materials. In this embodiment, the battery module 10 of FIG. 4B is three parallel chains of four ⅔ A size cells 14 of lithium manganese dioxide ($Li/MnO_2$). There is a current blocking devices 16, connected in series with each of the three parallel strings to prevent a reverse current or charging condition from another parallel string in the battery module 10. An example of cells 14 that can be utilized are Duracell® DL123A (manufactured by Duracell, Inc.) as described in FIG. 4A. Other cells 14 that would be appropriate would be obvious to one skilled in the art. As described previously, an appropriate current blocking device 16 is, for example, a diode and the current blocking device 16 can be located within a battery housing, and thus proximate to the battery cells 14, or it can be located in the receiving device housing.

This battery module 10 has a voltage of 12.0 Volts and a capacity of 4.2 Ah or 181 KJ. This battery module 10 of the preferred embodiment of FIG. 4B used in a biphasic defibrillator can deliver approximately 210 shocks as calculated from Equation (3) with $f_h=0.26$. This compares to about 130 shocks from the higher capacity and higher power battery modules 10 of FIGS. 2A, 3A, and 4A when used in a monophasic defibrillator with $f_h=0.26$.

Figure 4C:
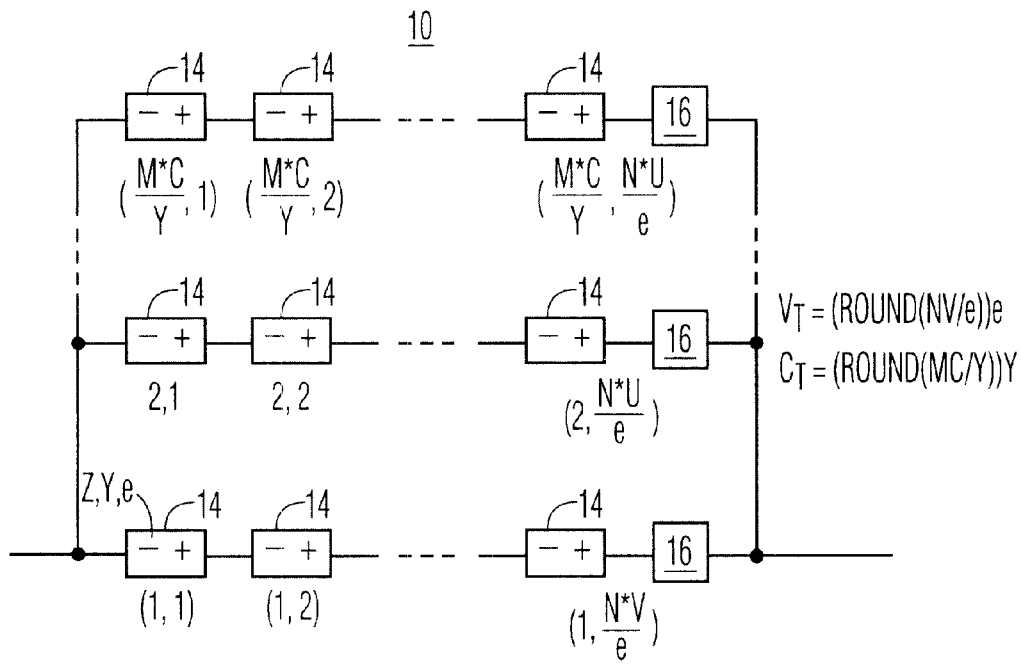
FIG. 4C is a block diagram of a generalized battery module according to the embodiment of FIG. 4A.

FIG. 4C shows a block diagram of a generalized battery module 10 constructed to the embodiment of the present invention shown in FIG. 4A. This battery module 10 replaces the prior art battery module 10 of FIG. 2B and takes advantage of a different battery chemistry. This battery module 10 is made of cells 14 each containing Z amount of active material, having a capacity Y at a voltage e. There is the rounded integer value of N*V/e cells 14 in series and the rounded integer value of M*C/Y cells 14 in parallel. The rounded integer values may have been rounded up or down depending on the size of the remainders. There is a current blocking device 16, connected in series with each of the parallel strings. A suitable current blocking device 16 is, for example, a diode and the current blocking device 16 can be located within a battery housing, and thus proximate to the battery cells 14, or it can be located in the receiving device housing. The battery module 10 has an output with a voltage of $V_T$=(round (NV/e))e and a capacity of $C_T$=(round (MC/Y))Y.

Figure 5:
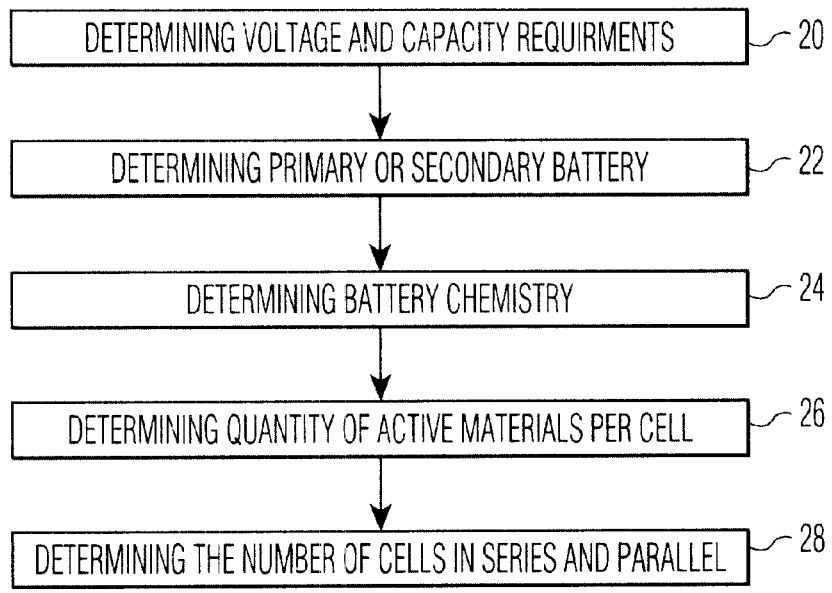
FIG. 5 is a flowchart of a method to optimize a battery module for safe operation.

A method of optimizing a battery module 10 for safe operation is shown in the flowchart of FIG. 5. Step 20 is determining the battery voltage and capacity requirements. The energy requirement of the device is considered. An example is described above for an AED and the battery capacity is given by Equation (3). Step 22 is determining whether a primary or secondary battery should be used. A factor to consider, for example, is the frequency of use of the device and whether the high maintenance of the secondary battery is justifiable. Step 24 is determining the battery chemistry. As stated earlier, there are many factors to consider when choosing the battery chemistry such as, for example, weight, cost, shelf life, toxicity, recyclability, and operating temperature range. Step 26 is determining the amount of active material per cell 14. The maximum rate at which current can be discharged, the internal resistance, and operating temperature should be considered for possible venting and explosion hazards. Another factor to consider, for example, is the environment in which the device may be operated. Special consideration must be given if the device is operated in a confined environment such as a mine, airplane, or automobile. If a cell of the battery module loses its contents in its environment of operation, will, for example, the PEL, TLV, LCLO, LC50 or LD50 be exceeded? If so, then a smaller cell size with less active material is dictated. Once the cell 14 size is chosen, step 28 is determining the number of cells 14 necessary in series and parallel and is determined according to Equations (1) and (2).

Conventional wisdom teaches to increase the amount of active materials in a battery cell 14, to decrease the number of cells 14 in a battery module 10, the total weight, and cost of the battery module 10. This invention teaches to limit the quantity of active materials in a battery cell 14 for applications where safety and reliability are of utmost importance, such as medical devices, the benefits far exceed cost and weight issues.

The present invention is an elegant solution to achieve safety and reliability in a battery module 10. There are many possible ways to configure and implement this invention. For instance, multiple battery modules 10 each containing smaller capacity cells 14 could be used. Protective circuitry, such as diodes to block reverse currents from individual cells 14, current and thermal fuses and switches, current limiting resistors may also be used with the invention. This protective circuitry can be external or internal to the battery cell. Primary (non-rechargeable) or secondary (rechargeable) cells 14 may be used in this invention.

I claim:

1. A battery module capable of delivering greater than 1 KJ comprising more than 6 electrically connected lithium cells, each lithium cell containing one of less than 2.0 grams of lithium and less than 10.0 grams of manganese dioxide, wherein the electrical connection is series, parallel, or both series and parallel, wherein the 6 electrically connected lithium cells having values of said one of less than 2.0 grams of lithium and less than 10.0 grams of manganese dioxide provides said greater than 1 KJ of energy with a reduced risk of injury to a user.

2. A battery module, as defined in claim 1, wherein the battery module is selected from the group consisting of primary and secondary.

3. A battery module capable of delivering greater than 85 KJ, comprising a plurality of electrically connected lithium cells, each lithium cell containing one of less than 2.0 grams of lithium and less than 10.0 grams of manganese dioxide, wherein the electrical connection is series, parallel, or both series and parallel.

4. A battery module, as defined in claim 3, wherein the battery module is selected from the group consisting of primary and secondary.

5. A battery module capable of delivering less than 84 KJ, comprising a plurality of electrically connected lithium cells, each lithium cell containing one of less than 2.0 grams of lithium and less than 10.0 grams of manganese dioxide, wherein the electrical connection is series, parallel, or both series and parallel.

6. A battery module, as defined in claim 5, wherein the battery module is selected from the group consisting of primary and secondary.

7. An external defibrillator, comprising:
   a battery module capable of delivering greater than 1 KJ, including,
      more than 6 electrically connected lithium cells, each lithium cell containing one of less than 2.0 grams of lithium and less than 10.0 grams of manganese dioxide, wherein the electrical connection is series, parallel, or both series and parallel; and
   wherein, the battery module provides power to the external defibrillator.

8. An external defibrillator, as defined in claim 7, wherein the external defibrillator delivers a biphasic waveform to a patient.

9. An external defibrillator, as defined in claim 7, wherein the battery module is selected from the group consisting of primary and secondary.

10. An external defibrillator, comprising:
    a battery module capable of delivering greater than 85 KJ, including,
       a plurality of electrically connected lithium cells, each lithium cell containing one of less than 2.0 grams of lithium and less than grams of manganese dioxide, wherein the electrical connection is series parallel, or both series and parallel,
    wherein, the battery module provides power to the external defibrillator, and wherein
       the plurality of electrically connected lithium cells having values of said one of less than 2.0 grams of lithium and less than 10.0 grams of manganese dioxide provides said greater than 85 KJ of energy with a reduced risk of injury to a user.

11. An external defibrillator, as defined in claim 10, wherein the external defibrillator delivers a biphasic waveform to a patient.

12. An external defibrillator, as defined in claim 10, wherein the battery module is selected from the group consisting of primary and secondary.

13. An external defibrillator, comprising:
    a battery module capable of delivering greater than 84 KJ, including,
       a plurality of electrically connected lithium cells, each lithium cell containing one of less than 2.0 grams of lithium and less than grams of manganese dioxide, wherein the electrical connection is series parallel, or both series and parallel, wherein, the battery module provides power to the external defibrillator, and wherein the plurality of electrically connected lithium cells having values of said one of less than 2.0 grams of lithium and less than 10.0 grams of manganese dioxide provides said greater than 85 KJ of energy with a reduced risk of injury to a user.

14. An external defibrillator, as defined in claim 13, wherein the external defibrillator delivers a biphasic waveform to a patient.

15. An external defibrillator, as defined in claim 13, wherein the battery module is selected from the group consisting of primary and secondary.

16. A battery module capable of delivering greater than 1 KJ, comprising a plurality of electrically connected lithium cells, each lithium cell containing one of less than 21 grams of sulfur dioxide and less than 15 grams of thionyl chloride, wherein the electrical connection is series, parallel, or both series and parallel.

17. An external defibrillator, comprising:

a battery module capable of delivering greater than 1 KJ, including, a plurality of electrically connected lithium cells, each lithium cell containing one of less than 21 grams of sulfur dioxide and less than 15 grams of thionyl chloride, wherein the electrical connection is series, parallel, or both series and parallel; and wherein, the battery module provides power to the external defibrillator.

18. An external defibrillator, as defined in claim 17, wherein the external defibrillator delivers a biphasic waveform to a patient.

\* \* \* \* \*